(12) United States Patent
Sigmon, Jr. et al.

(10) Patent No.: US 12,053,156 B2
(45) Date of Patent: Aug. 6, 2024

(54) ENDOSCOPE ROTATION MECHANISM

(71) Applicant: Cook Medical Technologies LLC, Bloomington, IN (US)

(72) Inventors: John C. Sigmon, Jr., Winston-Salem, NC (US); Michael J. Brecht, Pfafftown, NC (US); Christopher A. Carruthers, Winston-Salem, NC (US); Marc Spencer, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 28 days.

(21) Appl. No.: 17/325,895

(22) Filed: May 20, 2021

(65) Prior Publication Data

US 2021/0361149 A1 Nov. 25, 2021

Related U.S. Application Data

(60) Provisional application No. 63/028,172, filed on May 21, 2020.

(51) Int. Cl.
*A61B 1/00* (2006.01)
(52) U.S. Cl.
CPC ...... *A61B 1/00128* (2013.01); *A61B 1/00066* (2013.01); *A61B 1/00147* (2013.01)
(58) Field of Classification Search
CPC ............ A61B 1/00066; A61B 1/00071; A61B 1/00105; A61B 1/00112; A61B 1/00121; A61B 1/00183; A61B 2017/0046; A61B 2017/291
See application file for complete search history.

(56) References Cited

U.S. PATENT DOCUMENTS

| | | | | |
|---|---|---|---|---|
| 4,534,339 A | * | 8/1985 | Collins | A61B 1/00128 600/146 |
| 5,171,247 A | | 12/1992 | Hughett et al. | |
| 5,609,601 A | | 3/1997 | Kolesa et al. | |
| 5,634,466 A | * | 6/1997 | Gruner | A61B 1/0055 600/467 |
| 6,004,263 A | * | 12/1999 | Nakaichi | A61B 1/0607 600/179 |

(Continued)

FOREIGN PATENT DOCUMENTS

DE  102009060714 A1  6/2011
DE  10 2016 006155 A1  11/2017

(Continued)

OTHER PUBLICATIONS

Office Action in corresponding European Application No. 21732720.4 dated Jan. 4, 2023 (3 pages).

(Continued)

*Primary Examiner* — Ryan N Henderson
(74) *Attorney, Agent, or Firm* — Crowell & Moring LLP

(57) ABSTRACT

Disclosed herein is an endoscope system and a handle for a medical device that allows for rotation of the device when a locking member is disengaged by an operator, but does not allow for rotation when the locking member is engaged. Such a handle allows for an operator to maintain the position of an endoscope even when the operator removes his or her hand from the controls of the scope.

7 Claims, 13 Drawing Sheets

(56) References Cited

U.S. PATENT DOCUMENTS

| | | | |
|---|---|---|---|
| 6,228,059 B1 | 5/2001 | Astarita | |
| 6,250,532 B1 | 6/2001 | Green et al. | |
| 6,330,965 B1 | 12/2001 | Milliman et al. | |
| 7,192,396 B2 | 3/2007 | Boulais | |
| 7,212,737 B2* | 5/2007 | Dehmel | A61B 1/00126 |
| | | | 600/172 |
| 7,387,605 B2* | 6/2008 | Frith | A61B 1/042 |
| | | | 600/137 |
| 8,179,074 B2 | 5/2012 | Messerly et al. | |
| 8,475,362 B2* | 7/2013 | Sohn | A61B 1/00147 |
| | | | 600/137 |
| 9,107,573 B2* | 8/2015 | Birnkrant | A61B 1/00066 |
| 9,220,525 B2 | 12/2015 | Boebel et al. | |
| 9,307,891 B2* | 4/2016 | Carter | A61B 1/00042 |
| 9,700,289 B2 | 7/2017 | Prestel et al. | |
| 9,723,973 B2 | 8/2017 | Dillon et al. | |
| 10,709,315 B2 | 7/2020 | Gavalis et al. | |
| 11,642,007 B2* | 5/2023 | Shin | A61B 1/00105 |
| | | | 600/136 |
| 2002/0133077 A1 | 9/2002 | Edwardsen et al. | |
| 2004/0176691 A1 | 9/2004 | Edwardsen et al. | |
| 2006/0229495 A1* | 10/2006 | Frith | A61B 1/00128 |
| | | | 600/112 |
| 2007/0287993 A1 | 12/2007 | Hinman et al. | |
| 2009/0177039 A1* | 7/2009 | Frank | A61B 17/29 |
| | | | 74/504 |
| 2010/0331620 A1* | 12/2010 | Sohn | A61B 17/3423 |
| | | | 600/104 |
| 2014/0257253 A1 | 9/2014 | Jemison | |
| 2015/0148596 A1 | 5/2015 | Gitman | |
| 2019/0104932 A1 | 4/2019 | Truckai et al. | |
| 2020/0121284 A1 | 4/2020 | Schaer et al. | |
| 2020/0315625 A1 | 10/2020 | Hall et al. | |
| 2021/0068625 A1* | 3/2021 | Shin | A61B 1/0057 |
| 2021/0212556 A1* | 7/2021 | Nguyen | A61B 1/00066 |
| 2022/0007918 A1* | 1/2022 | Hameed | A61B 1/122 |
| 2023/0225587 A1* | 7/2023 | Park | A61B 1/00128 |
| | | | 600/136 |
| 2023/0225588 A1* | 7/2023 | Park | A61B 1/0052 |
| | | | 600/136 |
| 2023/0225591 A1* | 7/2023 | Ji | A61B 1/0057 |
| | | | 600/136 |

FOREIGN PATENT DOCUMENTS

| | | |
|---|---|---|
| WO | WO2008/144630 A2 | 11/2008 |
| WO | WO 2021/236881 A1 | 11/2021 |

OTHER PUBLICATIONS

Written Opinion of the International Preliminary Examining Authority for corresponding International Application No. PCT/US2021/033322 mailed Apr. 13, 2022, 6 pgs.

International Search Report and Written Opinion in corresponding PCT Application No. PCT/US2021/033322 mailed Aug. 27, 2021, 11 pages.

* cited by examiner

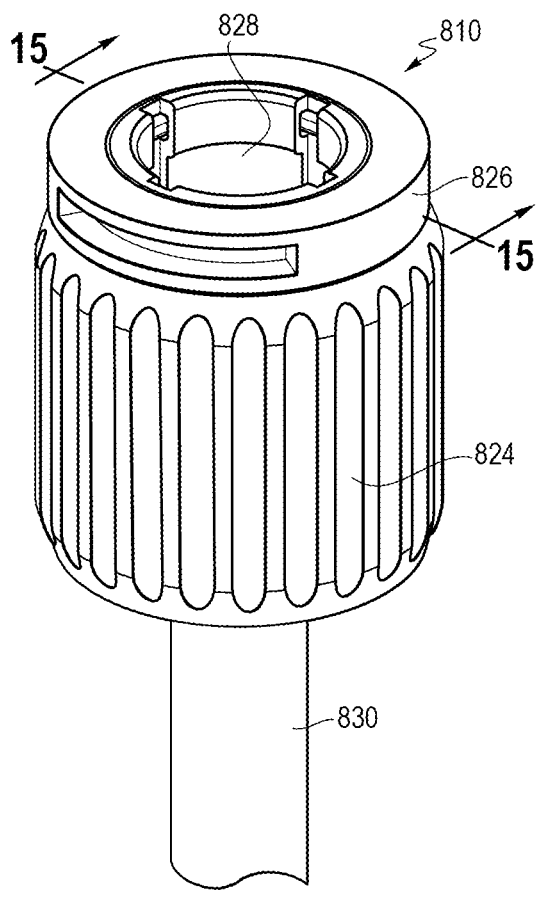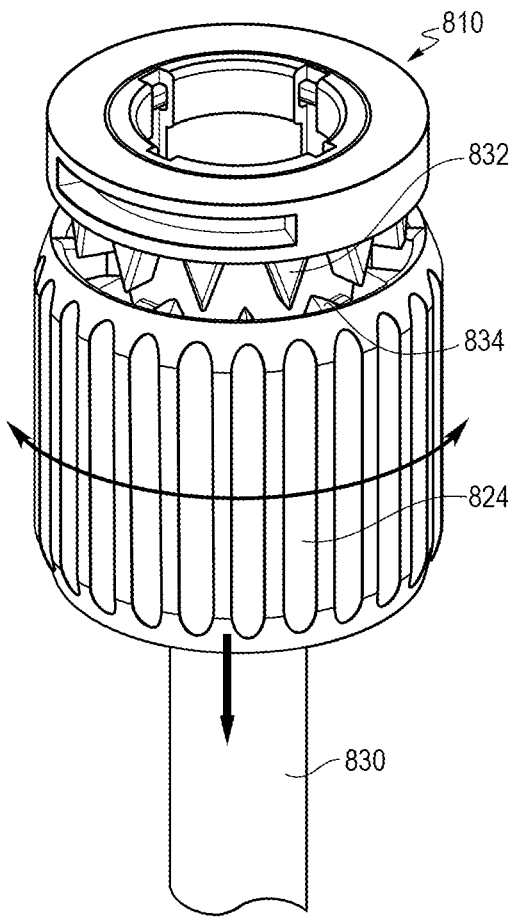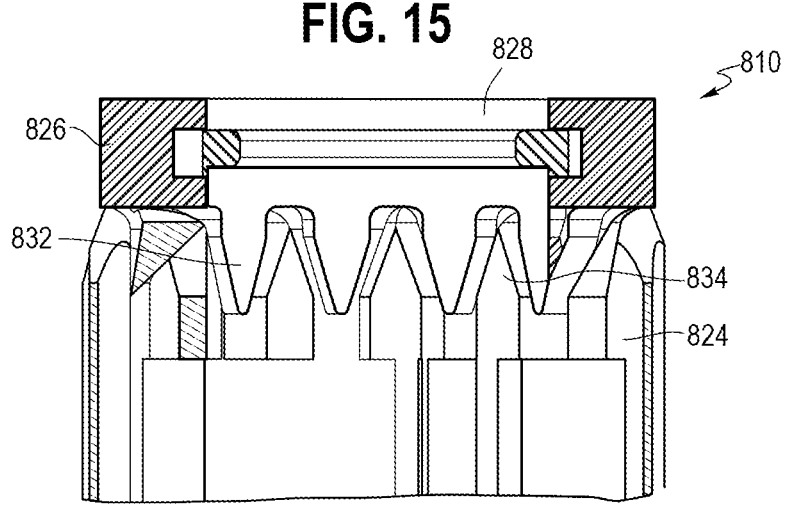

ENDOSCOPE ROTATION MECHANISM

CROSS-REFERENCE TO RELATED APPLICATIONS

This application claims priority from U.S. Provisional Application Ser. No. 63/028,172 filed on May 21, 2020, the entirety of which is hereby incorporated herein by reference.

FIELD

The present disclosure relates to medical devices. More particularly, the disclosure relates to handles for medical devices that allow for control over endoscope systems.

BACKGROUND

The statements in this section merely provide background information related to the present disclosure and may not constitute prior art.

Internal body cavities and body lumens may become blocked, or the walls surrounding them may develop growths. In some cases, removal of these blockages or growths, or other treatment thereof, may be necessary. Endoscopic or other minimally invasive techniques may be used to treat these situations.

One type of treatment includes the use of catheters or other endoscopic devices that are inserted into the body lumen or cavity and toward the area where treatment is desired. Insertion of the endoscope to the target area can allow for visualization of the target area and a determination of the desired procedure and the specific location of the area to be treated.

In general, endoscopes have been designed to be operated with the same fundamental mechanisms, and have not had transformational improvements. Endoscopes generally include a set of wheels that an operator, such as a physician, operates with a first hand (in some cases, the left hand) to control scope deflection, while the second (generally, right) hand switches between the insertion tube of the endoscope and the accessory channel in order to control scope and device advancement, respectively, through the anatomy of a patient.

Certain anatomical regions can be difficult to negotiate. For example, in the gastrointestinal (GI) tract, there are many bends, so that when the operator navigates to the target area, these bends cause the scope to rest in a specific orientation inside the lumen. During procedures like sphincterotomy or cancerous tissue resection, there may be certain approaches or scope orientations that may be more desirable so that the procedure is simpler, safer, and/or more effective.

For example, during sphincterotomy, a duodenoscope may be orientated by rotating the scope so that a papilla is located at approximately the 12 o'clock position prior to cannulation. However, keeping the scope in this orientation can be difficult when the operator needs to control a device at the accessory channel, as this involves letting go of the scope at the mouth or at the anus. In order to maintain the scope orientation, because the physician can no longer hold the scope, he or she must rotate his or her body away from the patient to maintain the torqued position. Not only is this uncomfortable for the physician after hours of endoscopy, it also means that the physician can only control one or the other of the scope and the tool/accessory channel, not both simultaneously.

During precise scope maneuvers, it may be desirable to advance the scope or the tool of the accessory channel incrementally by switching back and forth between the tool control and scope control. Maneuvers of this nature include, but are not limited to, cannulation of papilla and cutting tissue carefully to avoid bleeding or perforation. In such an instance, it can be considered that the physician effectively requires three hands rather than two to operate the scope.

SUMMARY

According to one aspect of the present disclosure, a handle for a medical device is provided. The handle includes an actuator configured to move between a locked configuration and an unlocked configuration. The actuator is biased to the locked configuration. The handle includes a catch configured to engage at least a portion of the actuator. The handle includes an elongate tube housing configured to receive an elongate tube. The elongate tube is configured to rotate relative to the handle and define a longitudinal axis therethrough. When the actuator is in the unlocked configuration, the actuator is disengaged from the catch, and the elongate tube is rotatable about the longitudinal axis relative to the handle, and when the actuator is in the locked configuration, the actuator engages with the catch, and the elongate tube is not rotatable about the longitudinal axis relative to the handle.

According to another aspect of the present disclosure, the handle includes an actuator configured to move between a locked configuration and an unlocked configuration. The actuator is biased to the locked configuration. The handle includes a catch having an outer surface and configured to engage at least a portion of the actuator. The handle includes a cavity configured to receive an elongate tube. The elongate tube is configured to rotate relative to the handle and defining a longitudinal axis therethrough. When the actuator is in the unlocked configuration, the actuator is disengaged from the catch, and the elongate tube is rotatable about the longitudinal axis relative to the handle, and when the actuator is in the locked configuration, the actuator engages with the catch, and the elongate tube is not rotatable about the longitudinal axis relative to the handle.

According to yet another aspect of the present disclosure, a scope system is provided. The scope system includes an elongate tube and a handle. The handle includes an actuator configured to move between a locked configuration and an unlocked configuration, the actuator being biased to the locked configuration. The handle includes a catch having an outer surface and configured to engage at least a portion of the actuator. The handle also includes a cavity configured to receive the elongate tube, the elongate tube being configured to rotate relative to the handle and defining a longitudinal axis therethrough. When the actuator is in the unlocked configuration, the actuator is disengaged from the catch, and the elongate tube is rotatable about the longitudinal axis relative to the handle. When the actuator is in the locked position, the actuator engages with the catch, and the elongate tube is not rotatable about the longitudinal axis relative to the handle.

According to yet another aspect of the present disclosure, a scope system is provided. The scope system includes an elongate tube and a handle. The handle includes an actuator configured to move between a locked configuration and an unlocked configuration, a catch having an outer surface configured to engage at least a portion of the actuator, and a cavity configured to receive the elongate tube such that the elongate tube is rotatable relative to the handle. The catch includes a stop for limiting rotation of the elongate tube relative to the handle. The elongate tube is rotatable relative to the handle over a range from greater than 0 degrees to less than 360 degrees.

According to yet another aspect of the present disclosure, a scope system is provided. The scope system includes an elongate tube and a handle. The handle includes an actuator configured to move between a locked configuration and an unlocked configuration, a catch configured to engage at least a portion of the actuator, and an elongate tube housing configured to receive the elongate tube such that the elongate tube is rotatable relative to the handle. The catch includes a stop for limiting rotation of the elongate tube relative to the handle. The elongate tube is rotatable relative to the handle over a range from greater than 0 degrees to less than 360 degrees.

Further areas of applicability will become apparent from the description provided herein. It should be understood that the description and specific examples are intended for purposes of illustration only and are not intended to limit the scope of the present disclosure.

DRAWINGS

In order that the present disclosure may be well understood, there will now be described various forms thereof, given by way of example, reference being made to the accompanying drawings. The components in the figures are not necessarily to scale. Moreover, in the figures, like-referenced numerals designate corresponding parts throughout the different views.

FIG. 13 illustrates a perspective view of an example of a rotation mechanism formed in accordance with the principles of the present disclosure;

FIG. 14 illustrates a perspective view of the example of the rotation mechanism of FIG. 13 with an actuator moved distally away from a catch;

FIG. 15 illustrates a longitudinal cross-sectional view of the rotation mechanism of FIG. 13;

Figure 1:
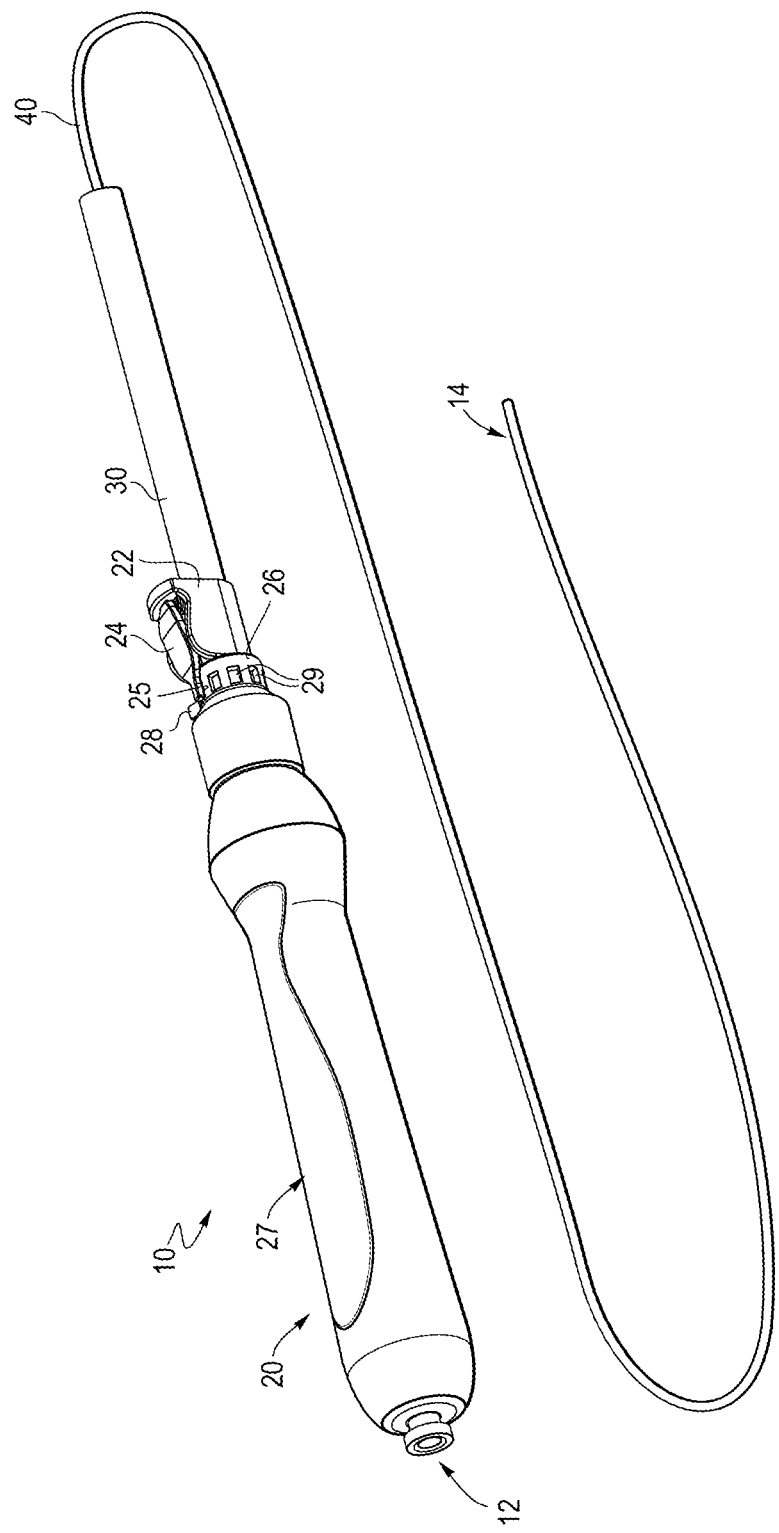
FIG. 1 illustrates a perspective view of an example of an endoscope system having a handle constructed according to the principles of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In adding reference denotations to elements of each drawing, although the same elements are displayed on a different drawing, it should be noted that the same elements have the same denotations. In addition, in describing one aspect of the present disclosure, if it is determined that a detailed description of related well-known configurations or functions blurs the gist of one aspect of the present disclosure, it will be omitted.

In the following discussion, the terms "proximal" and "distal" will be used to describe the opposing axial ends of the device, as well as the axial ends of various component features. The term "proximal" is used in its conventional sense to refer to the end of the device (or component) that is closest to the medical professional during use of the assembly. The term "distal" is used in its conventional sense to refer to the end of the device (or component) that is initially inserted into the patient, or that is closest to the patient during use. The term "longitudinal" will be used to refer to an axis that aligns with the proximal-distal axis of the device (or component). The terms "radially" and "radial" will be used to refer to elements, surfaces, or assemblies relative to one another that may extend perpendicularly from a longitudinal axis. The terms "circumference," "circumferentially," and "circumferential" will be used to refer to elements, surfaces, or assemblies relative to one another encircling a longitudinal axis at a radius.

The uses of the terms "a" and "an" and "the" and similar references in the context of describing the present disclosure (especially in the context of the following claims) are to be construed to cover both the singular and the plural, unless otherwise indicated herein or clearly contradicted by context. The use of the term "plurality of" is defined by the Applicant in the broadest sense, superseding any other implied definitions or limitations hereinbefore or hereinafter unless expressly asserted by the Applicant to the contrary, to mean a quantity of more than one. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein the terms "comprise(s)," "include(s)," "having," "has," "can," "contain(s)," and variants thereof, are intended to be open-ended transitional phrases, terms, or words that do not preclude the possibility of additional acts or structures. The present description also contemplates other embodiments "comprising," "consisting of" and "consisting essentially of," the examples or elements presented herein, whether explicitly set forth or not.

In describing elements of the present disclosure, the terms $1^{st}$, $2^{nd}$, first, second, A, B, (a), (b), and the like may be used herein. These terms are only used to distinguish one element from another element, but do not limit the corresponding elements irrespective of the nature or order of the corresponding elements.

Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art.

As used herein, the term "about," when used in the context of a numerical value or range set forth means a variation of ±15%, or less, of the numerical value. For example, a value differing by ±15%, ±14%, ±10%, or ±5%, among others, would satisfy the definition of "about," unless more narrowly defined in particular instances.

Referring to FIG. 1, an example of an endoscope system 10 is illustrated. The endoscope system 10 extends from proximal end 12 to distal end 14, and includes a handle 20. The endoscope system 10 also includes an elongate tube 30 which is engaged with the handle 20 such that it can rotate relative to the handle 20. The elongate tube 30 may be a flexible tube with at least one lumen 38 running throughout its length. In one aspect, the elongate tube 30 may be made of a braided material, such as a polyether block amide (including, for example, PEBAX) with a polytetrafluoroethylene ("PTFE") liner to provide sufficient torqueability and pushability. Other potential materials for the elongate tube 30 include, but are not limited to, polyethylene, polypropylene, and nylon.

The endoscope system 10 may further include at least one accessory channel 40 running through the elongate tube 30 and/or the handle 20. The accessory channels may be designed as individual elongated tubes that may be movable within the lumen 38 of the elongate tube 30, thus allowing longitudinal movement of the accessory channels 40 with respect to the elongate tube 30. When the elongate tube 30 is in a straight configuration, it defines a longitudinal axis running centrally therethrough, which represents the axis about which it may rotate relative to the handle 20. In practice, even when the elongate tube 30 is not in a straight configuration, the longitudinal axis is still defined at the same position, and the portion of the elongate tube 30 that is outside of the body of the patient and that substantially surrounds the longitudinal axis will be rotatable about said axis.

While one accessory channel 40 is illustrated in FIG. 1, an endoscope system 10 may include two accessory channels, three accessory channels, or more. For example, a single, larger accessory channel may be used to accommodate larger endoscopic tools. Further, in lieu of individual accessory channel(s) 40, a single elongate tube 30 may be used with two or channel lumens running through it. The accessory channels 40 may range in diameter anywhere from 0.5 millimeter to 20 millimeters, or from 1 millimeter to 10 millimeters. The accessory channels 40 may extend from proximal of or past the handle 20, through the lumen 38 and through the distal end 14. The accessory channels 40 may have an open end on both ends, and various tools, devices, and cameras may be inserted into and removed from the accessory channels 40. While the accessory channel 40 has been illustrated to extend well beyond the end of the elongate tube 30 in FIG. 1, this drawing is not necessarily to scale, and the elongate tube 30 may have a greater length.

Figure 2A:
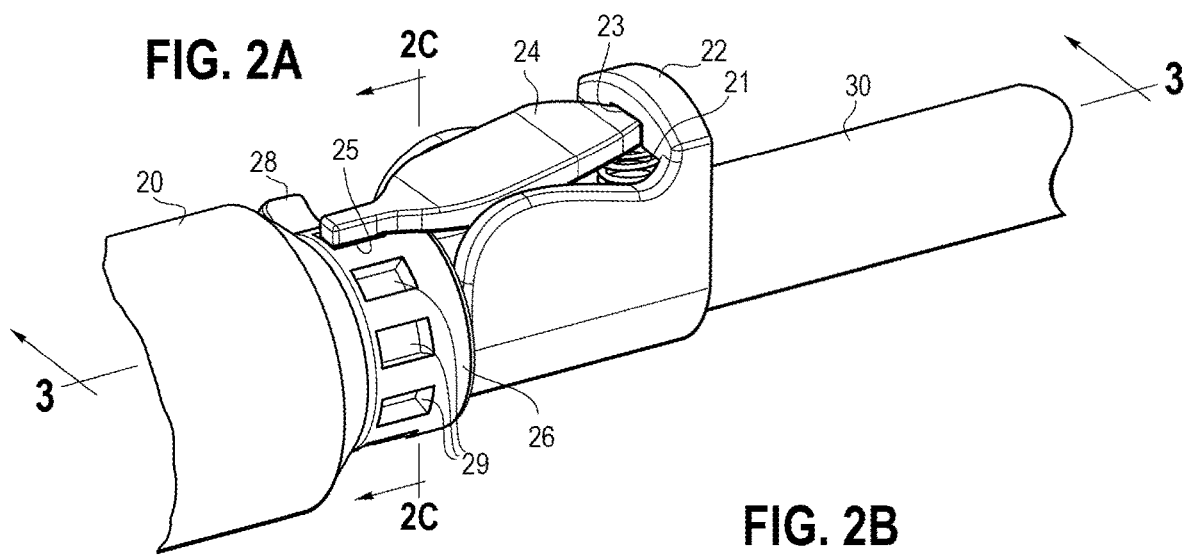
FIG. 2A illustrates a perspective view of an example of a handle having a locking mechanism in the engaged (locked) configuration.

FIG. 2A illustrates a closer view of the example of the handle 20 and its components. The handle 20 includes a catch 26. The catch 26 is configured to receive a portion of the actuator 24, which will be described in more detail. In the illustrated aspect, catch 26 is simply a distal portion of handle 20, which may be formed unitarily or monolithically with the proximal portion 27 that the operator grips.

To receive the actuator 24, in this aspect, the catch 26 defines detents 29 formed as indentations in its outer surface. Because the handle 20 is rotatable relative to the elongate tube 30, and locks in position when in contact with the actuator 24, the eight detents 29 as formed in the catch 26 as illustrated represent eight different locked positions for the endoscope system 10. Put another way, the locked configurations of the endoscope system 10 as illustrated in FIG. 2A represent a 45 degree rotation in each instance. However, it may be desirable to have another number of detents 29, according to the application for which the handle 20 and the endoscope system 10 is to be used. In some aspects, two detents 29, spaced 180 degrees apart, may be employed; or three detents 29, spaced 120 degrees apart; or four detents 29, spaced 90 degrees apart; or six detent 29, spaced 60 degrees apart; or 10 detents 29, spaced 36 degrees apart; or 15 detents 29, spaced 24 degrees apart; or 20 detents 29, spaced 18 degrees apart; or any number of detents 29 that may be desired.

Figure 2B:
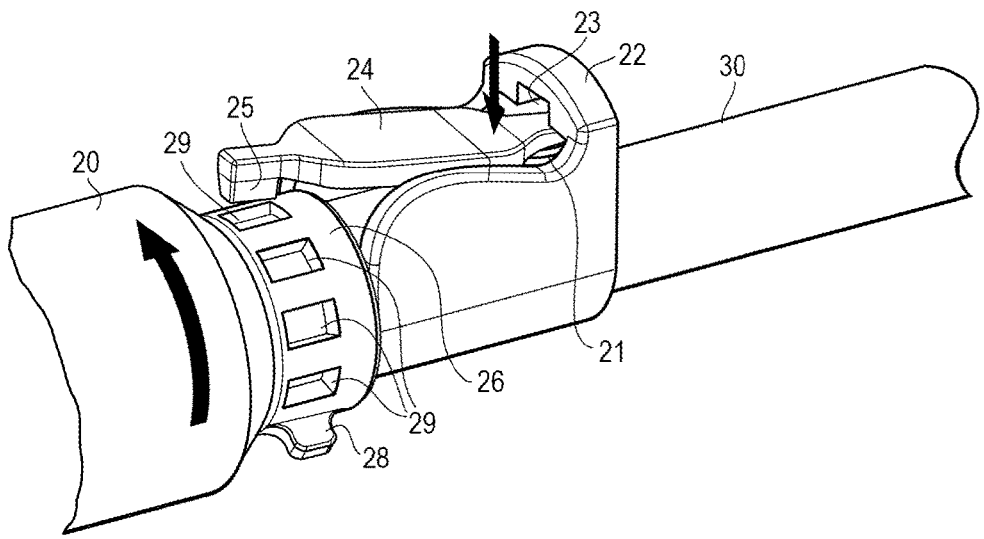
FIG. 2B illustrates a perspective view of the example of a handle of FIG. 2A with the locking mechanism in the disengaged (unlocked) configuration.

The actuator 24 of the endoscope system 10, as mentioned, engages with catch 26. As illustrated in FIG. 2A, the actuator 24 is provided in conjunction with housing 22, and can be moved by physical manipulation by a practitioner from an engaged (or locked) configuration as illustrated in FIG. 2A to a disengaged (or unlocked) configuration as illustrated in FIG. 2B. In the aspect illustrated, the practitioner may grip a more proximal portion 27 of handle 20 with the fingers, and hold the thumb over actuator 24, so that the actuator 24 can be depressed to move the endoscope system 10 from the locked configuration to the unlocked configuration, as illustrated by the motion arrow directed toward actuator 24. As illustrated by the motion arrow on handle 20 in FIG. 2B, the practitioner can rotate handle 20, which in turn allows the elongate tube 30 to rotate, when the endoscope system 10 is in the unlocked configuration.

Figure 2C:
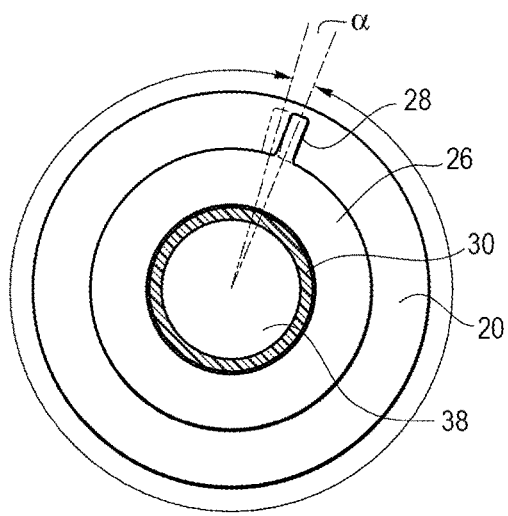
FIG. 2C illustrates an end view of the example of a catch of the handle of FIGS. 2A and 2B showing the rotational motion of the scope and the handle.

In some aspects, it may be desirable to limit the degree to which the handle 20 and the elongate tube 30 can rotate. For this reason, catch 26 may be shaped to have a projection 28 which extends radially outwardly therefrom. The projection 28, in the aspect illustrated in FIGS. 2A and 2B, juts out sufficiently so that if the handle 20 is rotated in a certain way, it will physically contact the pin 25 of actuator 24, which will inhibit or prevent further rotation about the longitudinal axis of the elongate tube 30. Limiting rotation can allow for more precise control of the final position of the scope within the patient. In a case where a projection 28 is provided, an endoscope system 10 can realize less than 360 degree rotation about the longitudinal axis of the elongate tube 30. In one aspect, the amount of rotation can be up to 359 degrees about the longitudinal axis, or greater than 0 degrees but up to or less than 359 degrees. The full extent of rotation is illustrated schematically in FIG. 2C, showing that projection 28 of catch 26 is rotatable about the center of the endoscope system 10, forming an angle between its initial position and its final position which can range from 0 degrees to 359 degrees.

The endoscope system 10 may include a housing 22 for the actuator 24, as illustrated in FIGS. 2A and 2B. The housing 22 is a distal portion of the handle 20 that may be formed separately from other components, such as the catch 26. The housing 22 may not be fixed to the elongate tube 30, or to the proximal portion 27 of the handle 20, so that the elongate tube 30 can rotate within the housing 22 when the actuator 24 is in the unlocked or disengaged configuration. Therefore, in at least one aspect, the housing 22 may be held in place when the operator depresses the actuator 24 toward the longitudinal axis, and the housing 22 then represents a portion of the handle 20 relative to which the elongate tube 30 rotates.

In another aspect, the endoscope system 10 may be constructed such that the actuator 24 rotates with (or does not rotate relative to) the proximal portion 27 of the handle 20. In this instance, the actuator 24 can serve a function similar to a switch: when the actuator 24 is depressed once, the elongate tube 30 is free to rotate; when it is depressed a second time, the actuator 24 re-engages with the elongate tube 30, locking it into place and stopping rotation. In another aspect, a secondary actuator or button may be provided (not shown) such that when the actuator 24 is depressed, the elongate tube 30 is free to rotate, and when the secondary actuator or button is depressed, rotation is stopped.

Figure 3:
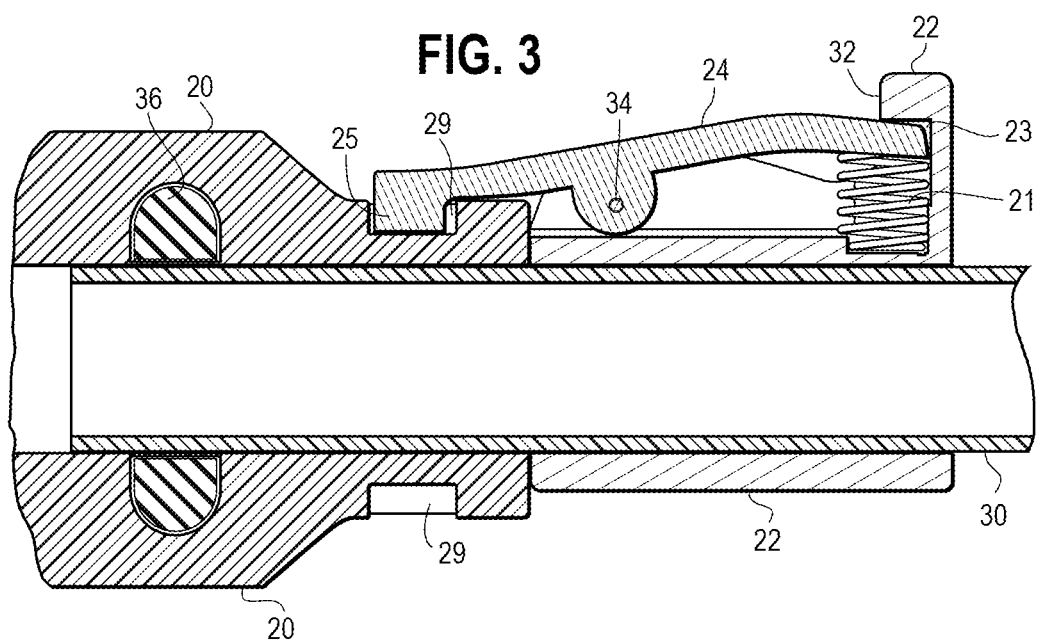
FIG. 3 illustrates a longitudinal cross-sectional view of an example of a handle and tube constructed in accordance with the principles of the present disclosure.

Turning now to FIG. 3, a longitudinal cross-sectional view of the example of endoscope system 10 is illustrated.

As can be seen in FIG. 3, the housing 22 provides a portion that fixes the actuator 24 to the housing 22, in this instance, rod 34. The operator can depress the actuator 24 about the rod 34, which serves as a pivot about which the actuator 24 can rotate. The actuator 24 may be biased to the locked configuration by spring 21, which may contact the actuator 24. The housing 22 may be formed with a slot 23 that may receive an end of the actuator 24 to define a maximal position away from the longitudinal axis of the elongate tube 30.

The actuator 24, in the aspect illustrated, engages with the catch 26 via pin 25, which extends toward the longitudinal axis at a proximal portion of the actuator 24. The pin 25 is sized to fit the detents 29.

Figure 4:
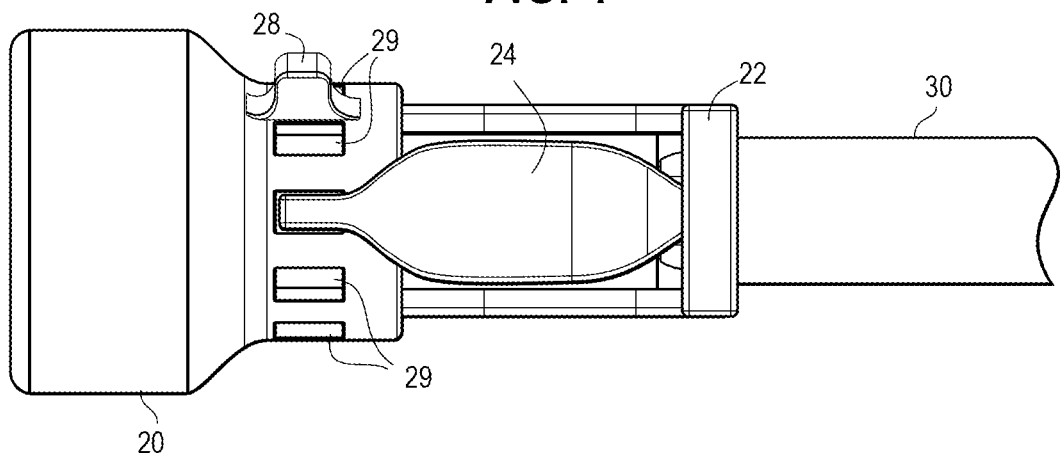
FIG. 4 illustrates a top view of the example of a handle and tube of FIG. 3.
Figure 5:
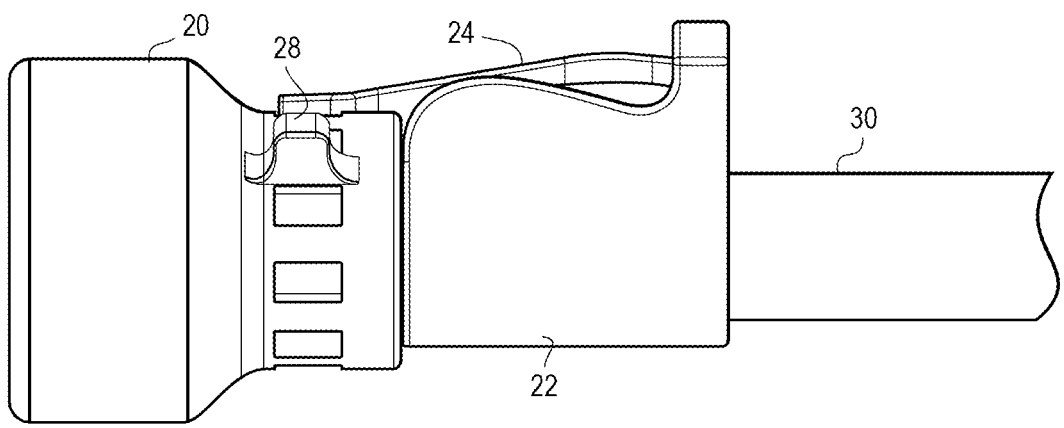
FIG. 5 illustrates a perspective side view of the example of a handle and tube of FIGS. 3 and 4.

The handle 20 may include a bearing 36 that defines an opening having a diameter sized to allow the elongate tube 30 to pass therethrough. The bearing 36 facilitates or eases rotation of the elongate tube 30 relative to the housing 22 of the handle 20 and provides responsive movement when the operator rotates the handle 20. FIGS. 4 and 5 illustrate additional perspective views of handle 20 of endoscope system 10.

Figure 6:
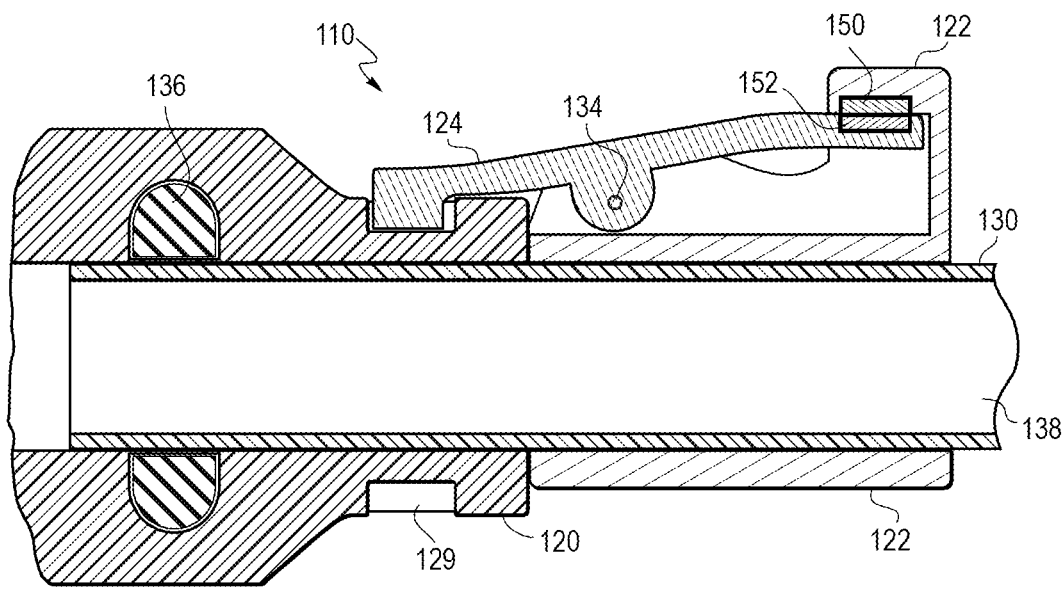
FIG. 6 illustrates a longitudinal cross-sectional view of another example of a handle constructed in accordance with the principles of the present disclosure.

The handle of the present disclosure can be constructed in a number of different ways. FIG. 6 illustrates another example of a handle 120 constructed according to the principles of the present disclosure. In this aspect, the actuator 124 includes a first magnet 152 disposed thereon at the distal end of the actuator 124, and engages with the housing 122, which includes a second magnet 150 disposed thereon. The first magnet 152 is attracted to second magnet 150, and thus no spring is included in this example of the system 110 because the attractive force between the first and second magnets 150, 152 biases the actuator 124 into the locked configuration.

In another aspect, the actuator 124 may include a first magnet at the pin portion, and instead of detents 129, the catch 126 may include a circular or ring-shaped magnet (not shown) to engage the pin of the actuator 124. Such a construction would allow for effectively infinite stop positions on the catch, allowing for small rotations even below one degree apiece, owing to the continuous shape of the ring magnet.

Figure 7:
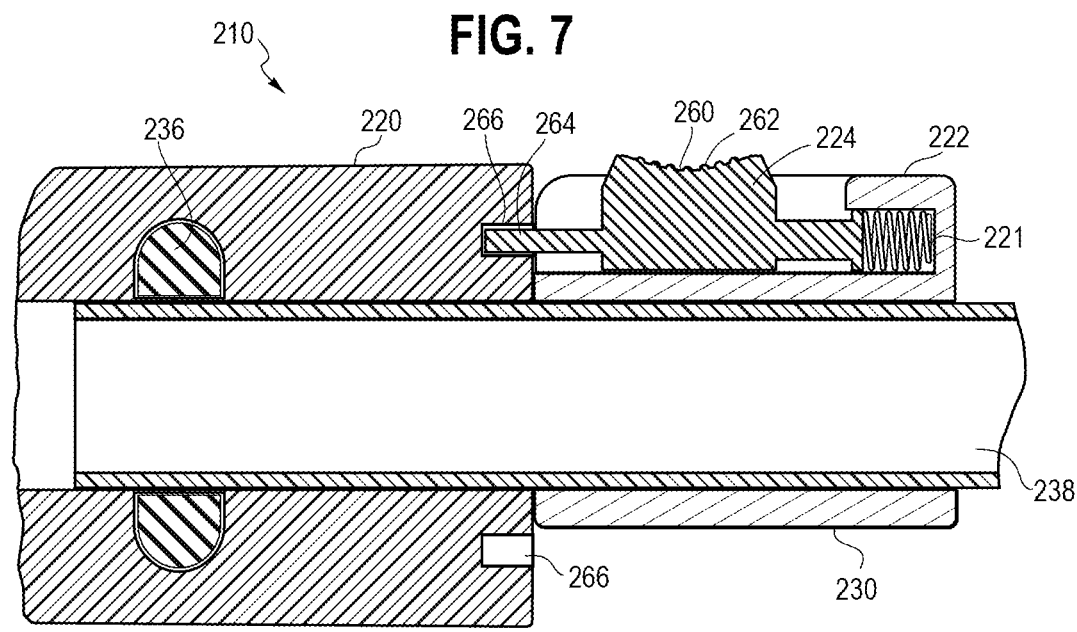
FIG. 7 illustrates a longitudinal cross-sectional view of another example of a handle with another example of an actuator, constructed in accordance with the principles of the present disclosure.

FIG. 7 illustrates another example of a locking mechanism of an endoscope system 210. In this aspect, handle 220 engages with sliding actuator 224 in the locked configuration. The sliding actuator 224 is biased to a proximal position at the proximal end of the handle 220 by spring 221, which is disposed substantially perpendicular to the longitudinal axis, and can be slid distally to a distal position, compressing the spring 221, in order to disengage the proximal end 264 of the actuator 224 from detent 266 and move the endoscope system 210 to the unlocked configuration. As illustrated in FIG. 7, the detents 266 in this example are formed in a distal face of the catch 226 rather than an outer surface thereof. The actuator 224 may have a contoured thumbrest 260 that may include ridges 262 to provide a textured surface for the operator's thumb.

Figure 8:
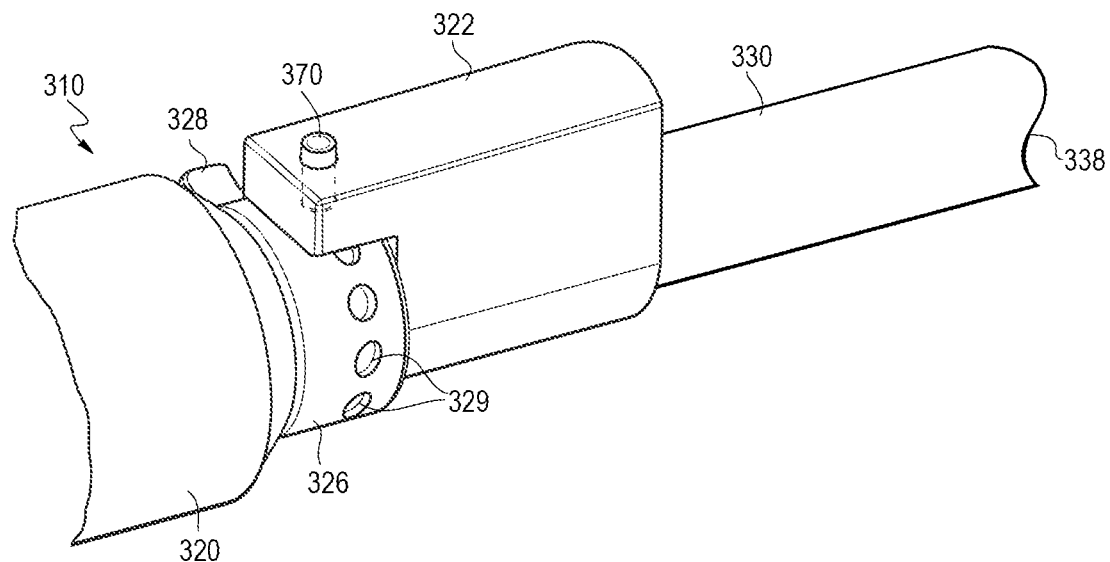
FIG. 8 illustrates a perspective view of an example of a portion of a handle with yet another example of an actuator.

FIG. 8 illustrates another example of a system 310 with a handle 320 constructed according to the principles of the present disclosure. In this example, the actuator 370 takes the form of a push button, having an end that can be press fit into the appropriately-shaped detents 329 formed in catch 326. The actuator 370 can be spring-loaded so that when the device is in the locked configuration, the actuator 370 can be further depressed and will spring out of the detent 329 it occupies to achieve the unlocked configuration. The housing 322 can be shaped with a taper toward its proximal end in order to allow a higher degree of rotation of handle 320.

Figure 9:
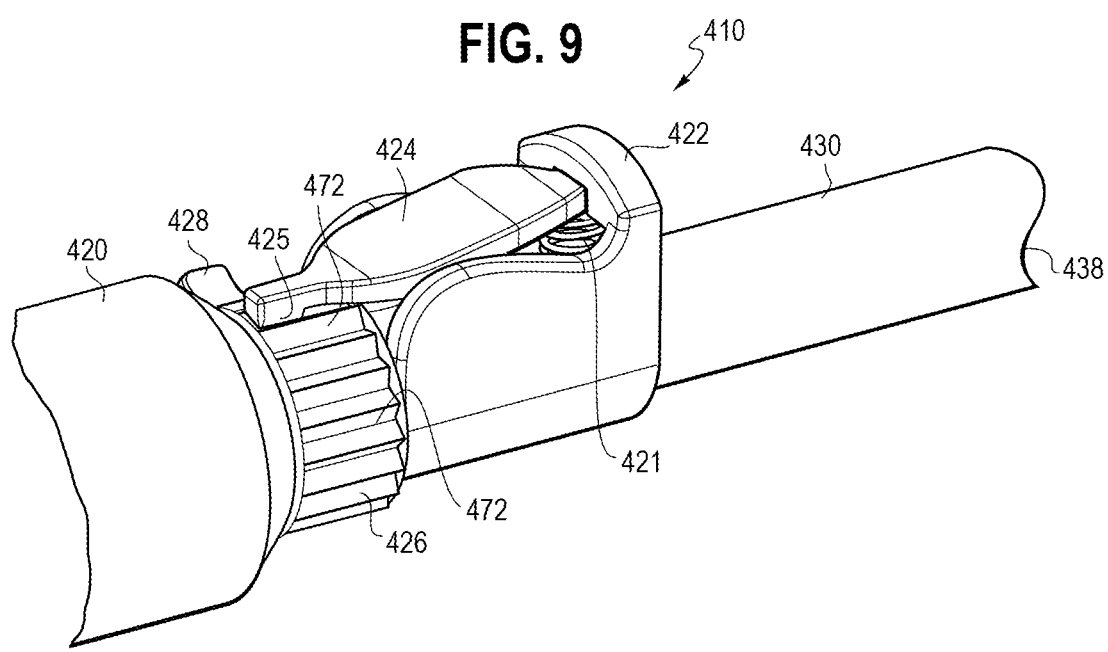
FIG. 9 illustrates a perspective view of an example of a portion of a handle having grooves and ridges formed on the catch.

In another variation, an example of a system 410 has an actuator 424 that is shaped similarly, or identical, to the examples of the actuator 24 illustrated in FIGS. 1-5. In the example of FIG. 9, actuator 424 engages catch 426 via grooves 472 which are disposed between ridges. The catch 426 may have a generally cylindrical shape. The ridges are substantially parallel ridges that run in a substantially proximal-to-distal direction, defining grooves 472 therebetween. The grooves 472 extend radially from the longitudinal axis about a circumference of an outer surface of catch 426 and each groove 472 runs in a substantially proximal-to-distal direction. As illustrated in FIG. 9, the ridges are defined at equal intervals about the circumference of catch 426, dividing the catch 426 into the desired number of rotational positions for the handle 420. As in other aspects, protrusion 428 may function as a mechanical stop that limits the rotation to under one full rotation, or less than 360 degrees. Protrusion 428 may physically contact the pin 425 of actuator 24, which will inhibit or prevent further rotation about the longitudinal axis of the elongate tube 430. Limiting rotation may allow for more precise control of the final position of the scope within the patient.

Figure 10:
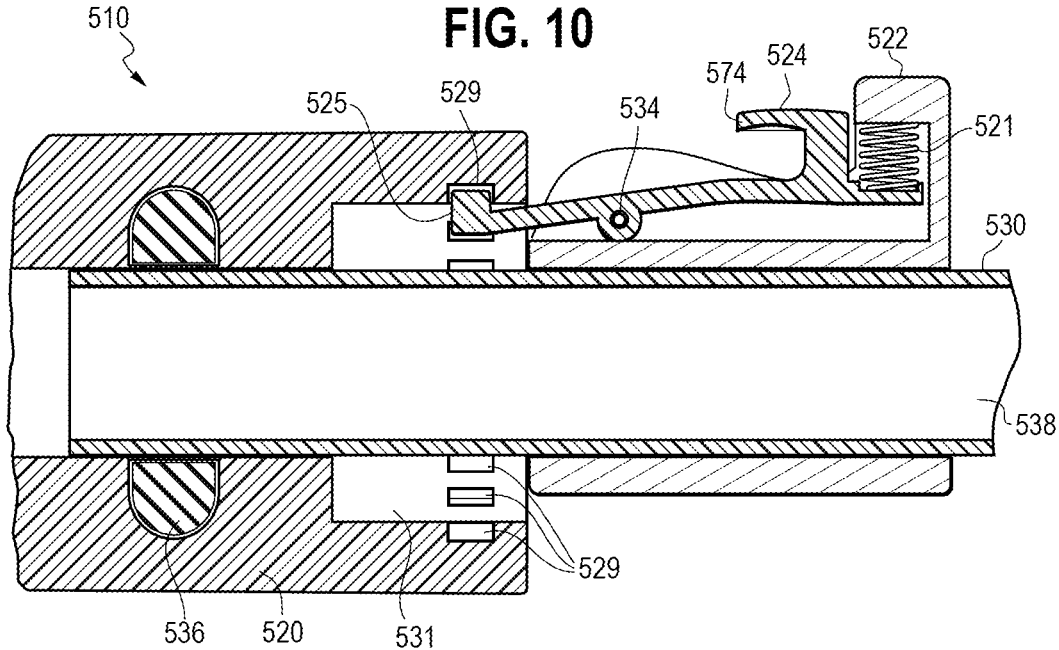
FIG. 10 illustrates a longitudinal cross-sectional view of an example of a handle having another example of a locking mechanism according to the principles of the present disclosure.

A further example of the system 510 is illustrated in FIG. 10. Here, the interior detents 529 are formed on an inner surface 531 of the handle 520, which functions as a catch, because the inner surface 531 of the handle 520 defines interior detents 529. The actuator 524 includes pin 525, which rests inside one of the interior detents 529 when the system 510 is in the locked configuration. The operator may use tactile cues, such as resistance to rotation even in the unlocked configuration, to determine where an interior detent 529 is relative to the location of pin 525 of the actuator 524.

Figure 11:
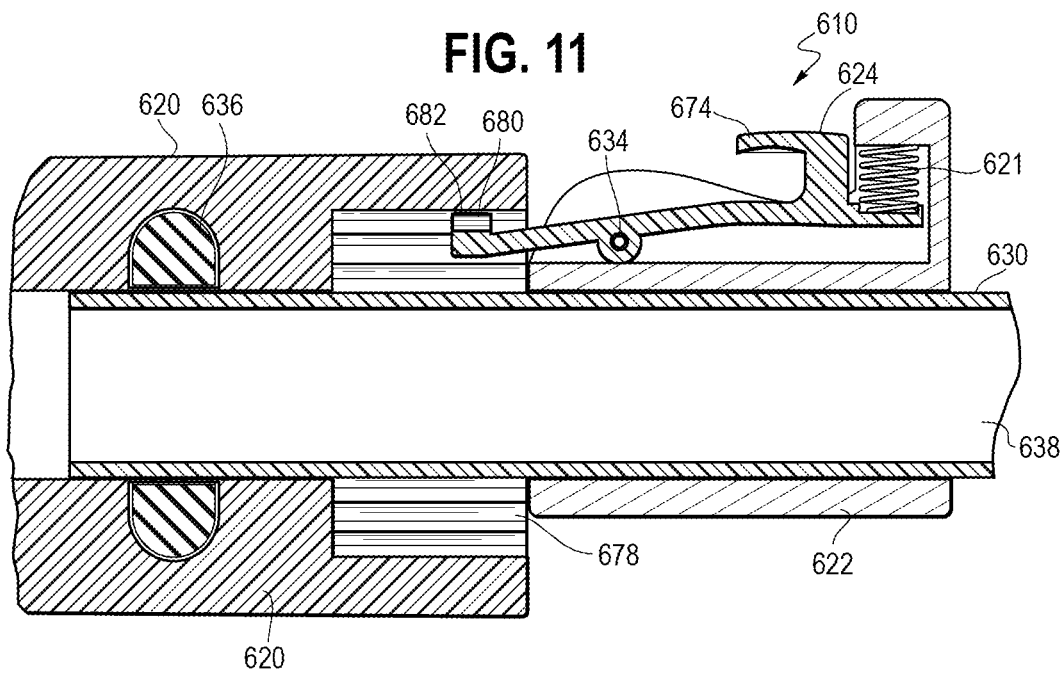
FIG. 11 illustrates a longitudinal cross-sectional view of an example of a handle having grooves and ridges formed in an interior portion of the handle.

The example illustrated in FIG. 11 combines features of the examples of the handles illustrated in FIG. 9 and FIG. 10. System 610 has handle 620, which includes an internal locking engagement arrangement, similar to what is illustrated in FIG. 10. However, in this variation, rather than individual detents, the interior portion is provided with ridges 682 and grooves 678, as in FIG. 9.

Figure 12:
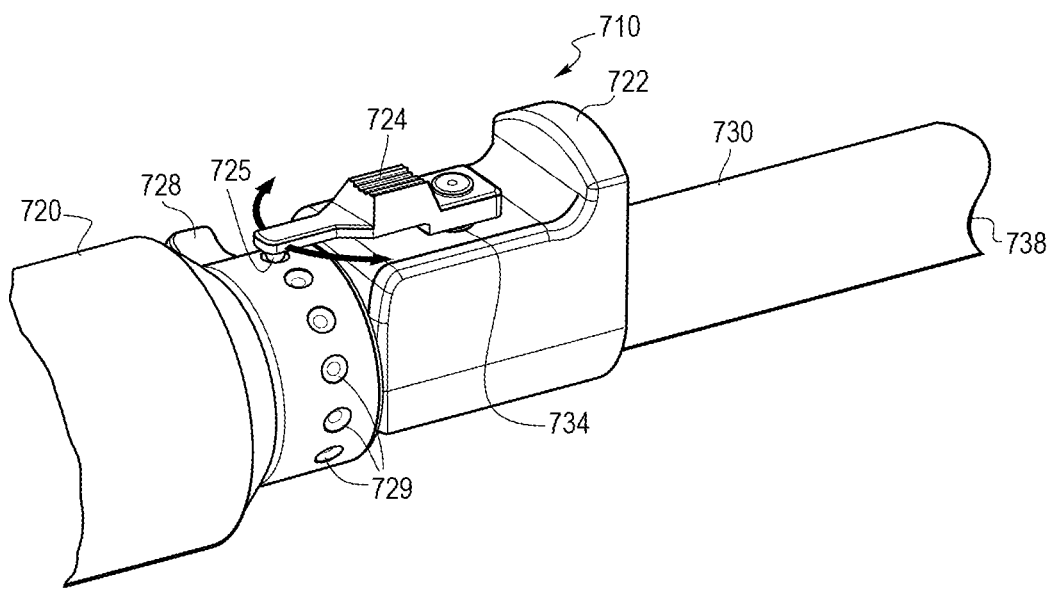
FIG. 12 illustrates a perspective view of an example of a handle having a swiveling actuator and formed in accordance with the principles of the present disclosure.

FIG. 12 illustrates another example of a handle 720 of a system 710 constructed in accordance with the principles of the present disclosure. In this example, the actuator 724 is a swivel mechanism, which the operator can move laterally, with rod 734 serving as a pivot. In some procedures, it may be desirable to make a lateral movement with the thumb, rather than a proximal-to-distal slide, or pressing toward the longitudinal axis. In this instance, swiveling the thumb laterally will cause pin 725 of actuator 724 to disengage from detent 729 of catch 726, thereby moving the system 710 from a locked configuration to an unlocked configuration. Swiveling the actuator 724 back toward center allows the system 710 to return to the locked configuration.

FIG. 13 illustrates a perspective view of an example of a rotation mechanism 810 formed in accordance with the principles of the present disclosure. In this example, elongate tube connector 828 is connected to catch 826 such as to prevent distal-proximal translation of catch 826 relative to elongate tube connector 828, but such as to provide for unconstrained circumferential rotation of catch 826 and elongate tube connector 828 relative to each other. Elongate tube 830 is rigidly connected to elongate tube connector 828 such as to prevent distal-proximal translation and rotation of elongate tube 830 relative to elongate tube connector 828. Actuator 824 is connected to elongate tube connector 828 to prevent rotation of actuator 824 relative to elongate tube connector 828, but such as to provide for translation of actuator 824 distally relative to elongate tube connector 828 and catch 826. Actuator 824 may have a radial outward surface that is at least partially textured (as shown in FIG. 13) so as to allow the operator to translate actuator 824 distally, or provide non-zero torque to actuator 824, with the operator's thumb or other finger. Actuator 824 is shown in a locked configuration in FIG. 13, and is biased to the locked configuration. In the locked configuration, elongate tube 830 is not rotatable about the longitudinal axis relative to a mechanism grip or handle.

FIG. 14 illustrates a perspective view of rotation mechanism 810. In FIG. 14, actuator 824 is translated distally relative to elongate tube connector 828 and catch 826. When actuator 824 is translated distally relative to elongate tube connector 828 and catch 826, actuator 824 is in an unlocked configuration, in which a plurality of actuator teeth 834 that may be disposed about the proximal inner circumference of actuator 824 are disengaged from a plurality of catch teeth 832. The plurality of catch teeth 832 may be disposed about the distal circumference of catch 826. When actuator 824 is in an unlocked configuration, the operator may rotate actuator 824 circumferentially by applying torque, thereby rotating elongate tube connector 828 and elongate tube 830 relative to catch 826. When the operator releases actuator 824, actuator 824 moves proximally back into the locked configuration as shown in FIG. 13. Plurality of actuator teeth 834 have a mating geometry with plurality of catch teeth 832, such that in the locked configuration, plurality of actuator teeth 834 mesh with plurality of catch teeth 832 so as to prevent rotation of elongate tube 830 about the longitudinal axis relative to a mechanism grip or handle.

In another example (not shown), teeth of the catch and/or the actuator may have a mating geometry between the teeth of the catch and the teeth of the actuator such that when the operator applies torque to the actuator or to the elongate tube, the torque may cause the mating geometry to translate the actuator distally between locked and unlocked configurations without the operator applying distal force. Teeth of the actuator and teeth of the catch may have a non-zero angle or a plurality of detents. A "zero angle" will be used to refer to a circumference perpendicular to the longitudinal axis. A "non-zero angle" will be used to refer to all angles other than a zero angle as defined herein.

FIG. 15 illustrates a longitudinal cross-sectional view of rotation mechanism 810 along bisection 15 in FIG. 13. As shown in FIG. 15, actuator 824 is in a locked configuration and plurality of actuator teeth 834 have a mating geometry with plurality of catch teeth 832 such that plurality of actuator teeth 834 are meshed with plurality of catch teeth 832.

Figure 16:
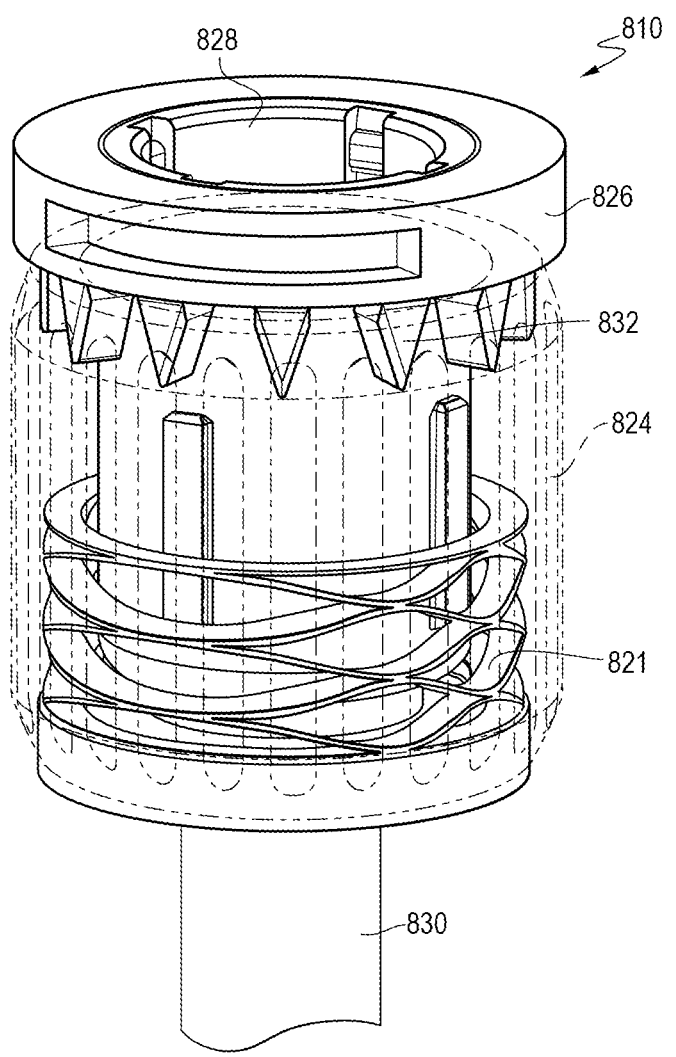
FIG. 16 illustrates a perspective view of the example of the rotation mechanism of FIG. 13 with an actuator shown as see-through in order to show a spring within the actuator.

FIG. 16 illustrates a perspective view of rotation mechanism 810 with actuator 824 shown as see-through or transparent for purposes of illustration. Spring 821 is positioned about the circumference of rotation mechanism 810 internal to actuator 824. Spring 821 biases actuator 824 into the locked configuration such that plurality of actuator teeth 834 are meshed with plurality of catch teeth 832 and elongate tube 830 is prevented from rotating about the longitudinal axis relative to a mechanism grip or handle.

Figure 17:
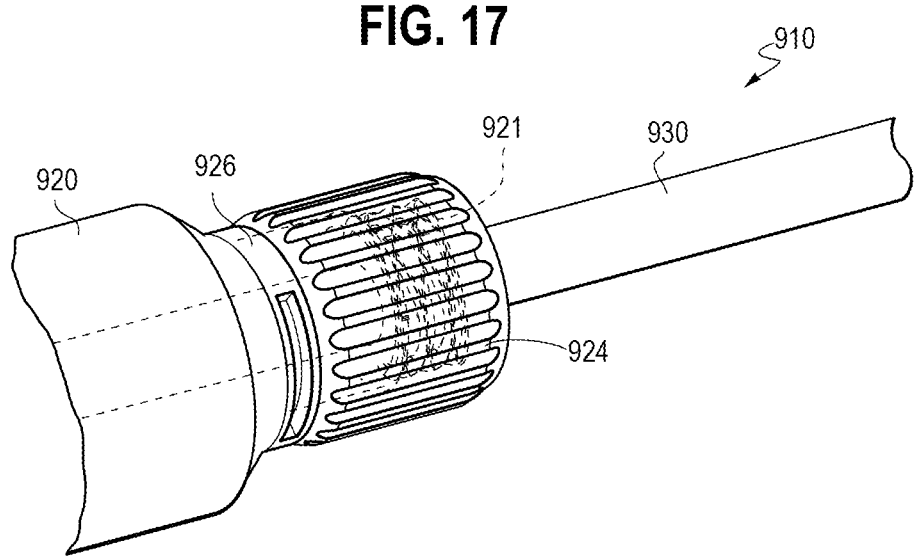
FIG. 17 illustrates a perspective view of an example of a handle having the rotation mechanism of FIG. 13 with the actuator shown as see-through to show the spring within the actuator.

FIG. 17 illustrates another example of a handle 920 of a system 910 constructed in accordance with the principles of the present disclosure. In this example, an elongate tube connector (not shown) is connected to catch 926 as illustrated in FIG. 13 for elongate tube connector 828 and catch 826 such as to prevent distal-proximal translation of distal-proximal translation of catch 926 relative to the elongate tube connector, but such as to provide for unconstrained circumferential rotation of catch 926 and the elongate tube connector relative to each other. Elongate tube 930 is rigidly connected to the elongate tube connector such as to prevent distal-proximal translation and rotation of elongate tube 930 relative to the elongate tube connector. Actuator 924 is connected to the elongate tube connector to prevent rotation of actuator 924 relative to the elongate tube connector, but such as to provide for translation of actuator 924 distally relative to the elongate tube connector and catch 926. Actuator 924 may have a radially outward surface that is at least partially textured (as shown in FIG. 17) so as to allow the operator to translate actuator 924 distally, or provide non-zero torque to actuator 924, with the operator's thumb or other finger. Actuator 924 is shown in a locked configuration in FIG. 17, and is biased to the locked configuration. In the locked configuration, elongate tube 930 is not rotatable about the longitudinal axis relative to handle 920. In FIG. 17, actuator 924 is shown as see-through or transparent for purposes of illustration. Spring 921 is positioned about the circumference internal to actuator 924. Spring 921 biases actuator 924 into the locked configuration with proximal end of actuator 924 confronting distal end of catch 926.

Figure 18:
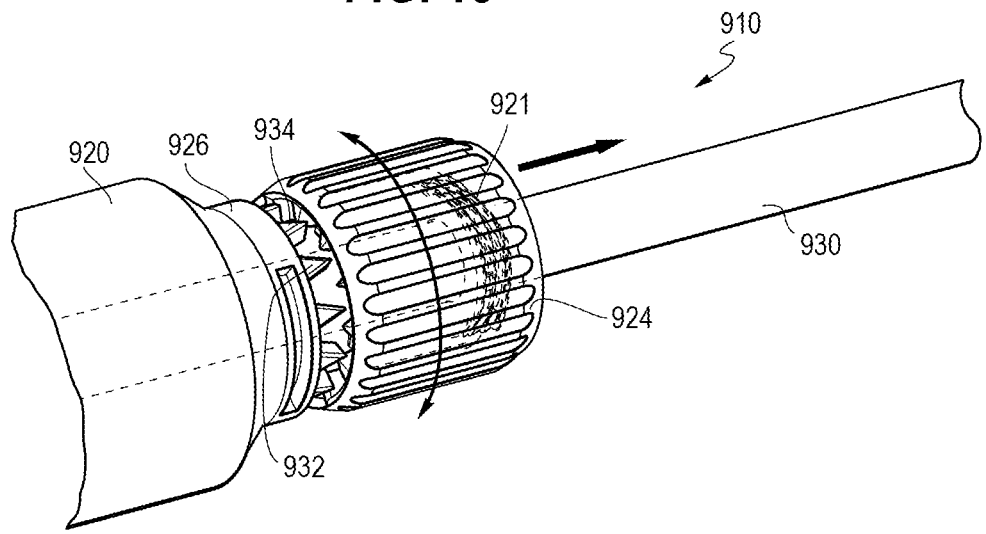
FIG. 18 illustrates a perspective view of the example of the handle of FIG. 17 with the actuator shown as see-through, the actuator moved distally away from the catch to compress the spring within the actuator.

FIG. 18 illustrates a perspective view of the example of handle 920 of system 910. In FIG. 18, actuator 924 is translated distally relative to the elongate tube connector and catch 926. When actuator 924 is translated distally, actuator 924 is in an unlocked configuration, in which a plurality of actuator teeth 934 that may be disposed about the proximal inner circumference of actuator 934 are disengaged from a plurality of catch teeth 932 and spring 921 is compressed. When actuator 924 is in an unlocked configuration, the operator may rotate actuator 924 circumferentially by applying torque, thereby rotating elongate tube 930 and the elongate tube connector relative to catch 926. Plurality of catch teeth 932 may be disposed about the distal circumference of catch 926. When the operator releases actuator 924, spring 921 is released, thereby moving actuator 924 proximally back into the locked configuration as shown in FIG. 17. Plurality of actuator teeth 934 have a mating geometry with plurality of catch teeth 932 such that in the locked configuration, plurality of actuator teeth 934 mesh with plurality of catch teeth 932 so as to prevent rotation of elongate tube 930 about the longitudinal axis relative to handle 920.

In another example (not shown), teeth of the catch and/or the actuator may have a mating geometry between the teeth of the catch and the teeth of the actuator such that when the operator applies torque to the actuator or the elongate tube, the torque may cause the mating geometry to translate the actuator distally without the operator applying distal force. Teeth of the catch and teeth of the actuator may have a non-zero angle or a plurality of detents.

Figure 19:
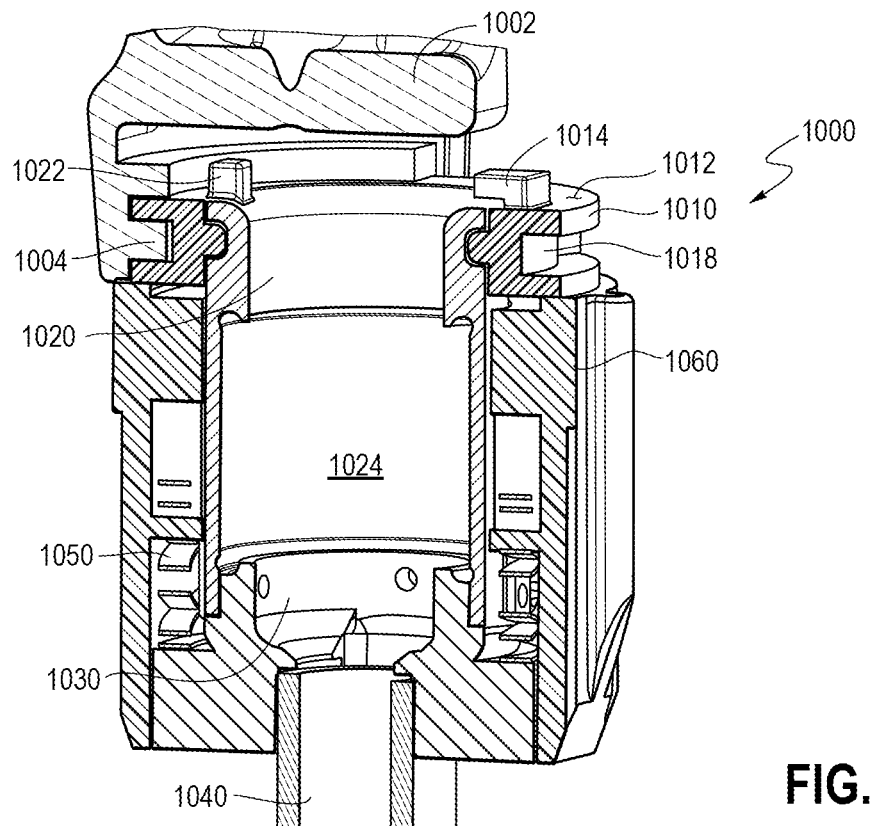
FIG. 19 illustrates a longitudinal cross-sectional view of another example of a rotation mechanism and handle formed in accordance with the principles of the present disclosure.

FIG. 19 illustrates a longitudinal cross-sectional view of another example of a rotation mechanism 1000 and handle 1002 formed in accordance with the principles of the present disclosure. In this example, elongate tube housing 1030 is configured to receive the proximal end of elongate tube 1040. In a proximal to distal direction, inner collar 1020 confronts the inner radial surface of catch 1010, actuator 1060, and spring 1050, and the proximal end of elongate tube housing 1030. Inner collar 1020 is rigidly connected to elongate tube housing 1030, and elongate tube housing 1030 is rigidly connected to elongate tube 1040 such as to prevent distal-proximal translation and rotation of inner collar 1020 relative to elongate tube housing 1030 and elongate tube 1040, distal-proximal translation and rotation of elongate tube housing 1030 relative to inner collar 1020 and elongate tube 1040, and distal-proximal translation and rotation of elongate tube 1040 relative to inner collar 1020 and elongate tube housing 1030.

Figure 24:
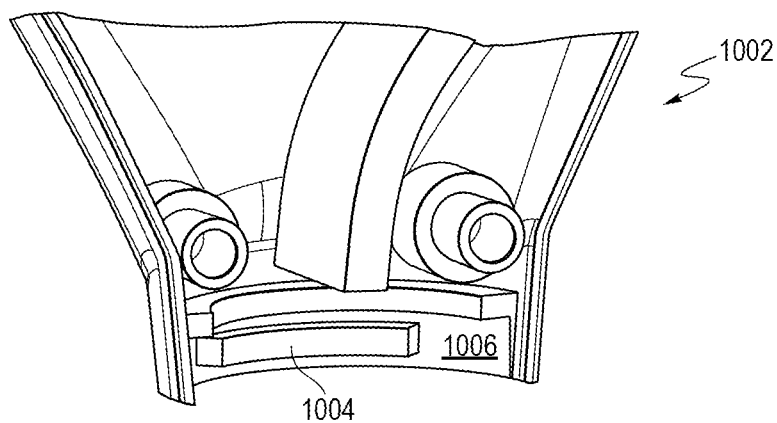
FIG. 24 illustrates a longitudinal cross-sectional view of the handle of FIG. 19.
Figure 25:
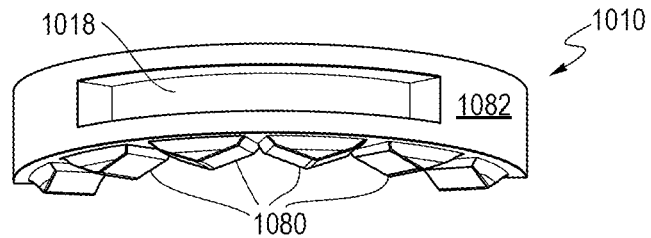
FIG. 25 illustrates a perspective view of the catch of FIG. 19.

Actuator 1060 is shown in a locked configuration in FIG. 19, and is biased to the locked configuration by spring 1050. In the locked configuration, actuator 1060, inner collar 1020, elongate tube housing 1030, and elongate tube 1040 are not rotatable about the longitudinal axis relative to catch 1010 or handle 1002. When actuator 1060 is in an unlocked configuration, due to the application of distal force or non-zero torque to actuator 1060, actuator 1060, inner collar 1020, elongate tube housing 1030, and elongate tube 1040 are rotatable about the longitudinal axis relative to catch 1010 and handle 1002. Inner collar 1020 includes stop 1022 extending proximally from the proximal surface of inner collar 1020. Catch 1010 includes protrusion 1014 extending proximally from proximal surface 1012 of catch 1010 and radially inwardly toward radial inner surface 1024 of inner collar 1020 such that protrusion 1014 is configured to confront stop 1022 during rotation of inner collar 1020 and thereby prevent complete 360-degree rotation of inner collar 1020, actuator 1060, elongate tube housing 1030, and elongate tube 1040 relative to catch 1010 and handle 1002. In other examples (not shown), the proximal surface of the catch may include a stop while the proximal surface of the inner collar includes a protrusion, the protrusion extending radially outward and configured to confront the stop and thereby prevent complete 360-degree rotation of the inner collar, the actuator, the elongate tube housing, and the elongate tube relative to the catch and the handle. Catch 1010 includes one or more radially-inward apertures 1018 in the radial outward surface of catch 1010. Handle 1002 includes one or more projections 1004 extending radially inwardly from radially inward surface 1006 of handle 1002, as shown in FIG. 24, configured to match aperture(s) 1018, as shown in FIG. 25, so as to prevent rotation of handle 1002 relative to catch 1010.

Figure 20:
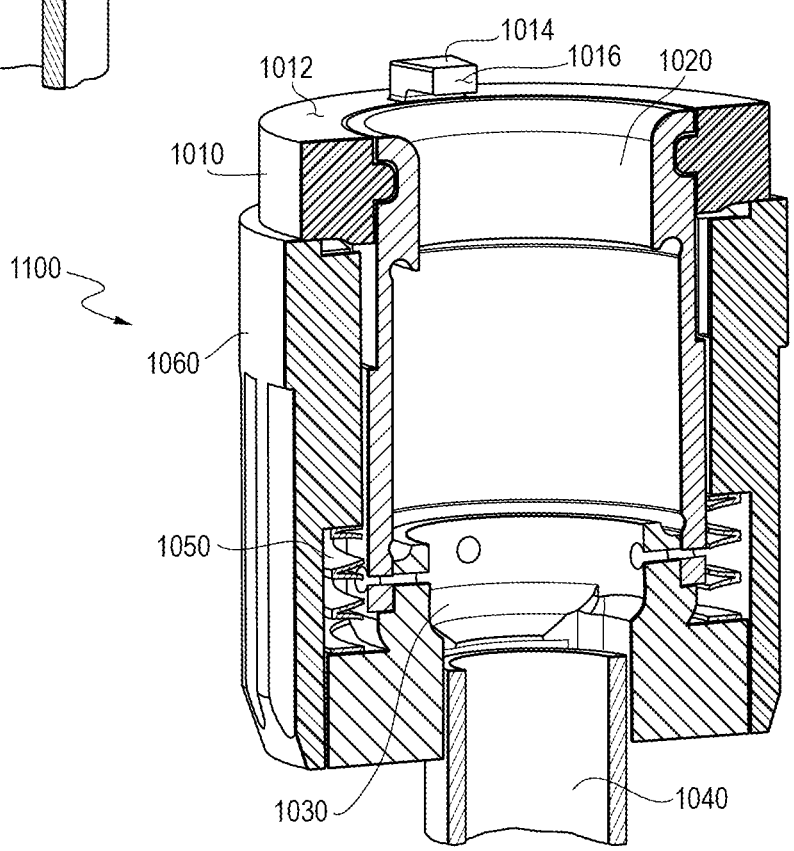
FIG. 20 illustrates a longitudinal cross-sectional view of the catch, inner collar, spring, actuator, elongate tube, and elongate tube housing assembly of FIG. 19.

FIG. 20 illustrates a longitudinal cross-sectional view of catch 1010, inner collar 1020, spring 1050, actuator 1060, elongate tube 1040, and elongate tube housing 1030 assembly of FIG. 19. Protrusion 1014 includes radially-inward surface 1016 that may extend further radially inward than radially inward surface 1024 of inner collar 1020.

Figure 21:
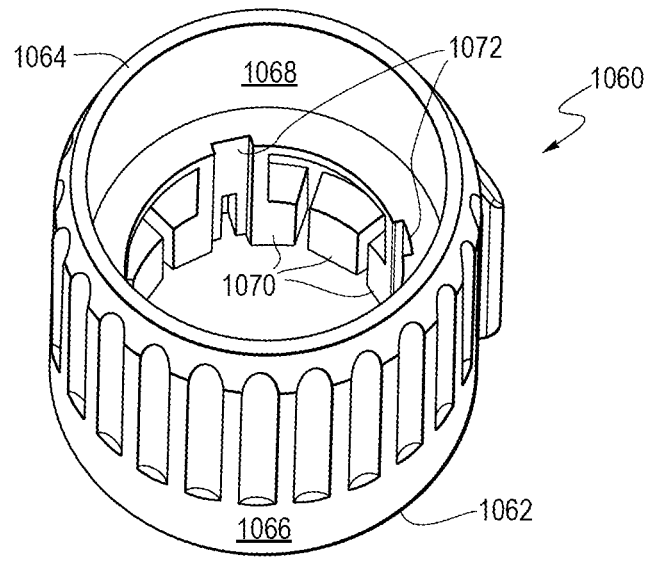
FIG. 21 illustrates a perspective view of the actuator of FIG. 19 with the distal end of the actuator shown at the top of FIG. 21 and the proximal end of the actuator at the bottom of FIG. 21.

FIG. 21 illustrates a perspective view of actuator 1060 of FIG. 19 with distal end 1064 of actuator 1060 shown at the top of FIG. 21 and proximal end 1062 of actuator 1060 shown at the bottom of FIG. 21. At least a portion of radially outward surface 1066 of actuator 1060 may be textured (as shown in FIG. 21), so as to allow the operator to translate actuator 1060 distally, or provide non-zero torque to actuator 1060, with the operator's thumb or other finger. Radially inward surface 1068 of actuator 1060 may include one or more proximal-distal slots 1072 extending distally from proximal end 1062. A plurality of actuator teeth 1070 extending proximally are disposed about the inner circumference of proximal end 1062.

Figure 22:
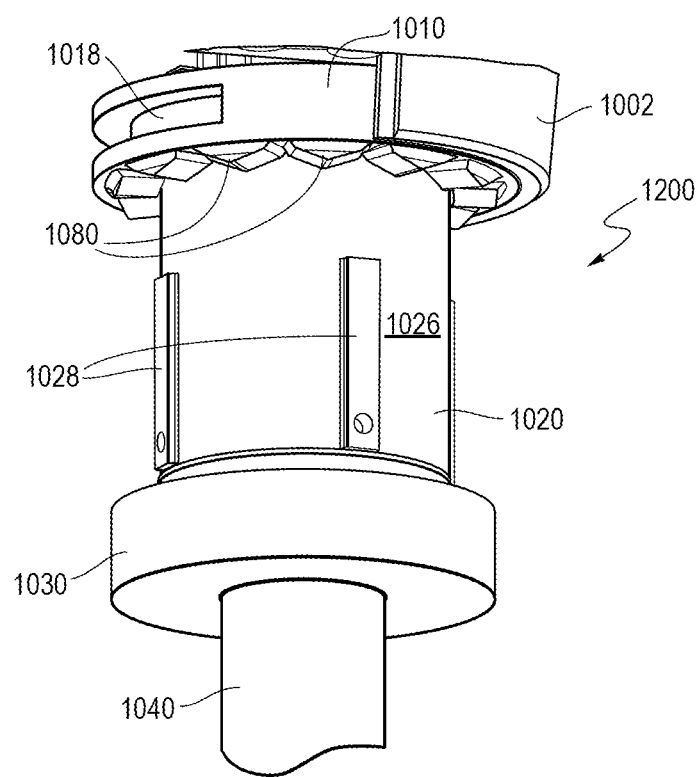
FIG. 22 illustrates a perspective view of the catch, inner collar, elongate tube, and elongate tube housing assembly of FIG. 19.

FIG. 22 illustrates a perspective view of handle 1002, catch 1010, inner collar 1020, elongate tube 1040, and elongate tube housing 1030 assembly of FIG. 19 including a cross-section cutaway view of handle 1002. Catch 1010 includes a plurality of catch teeth 1080 extending distally from the distal surface of catch 1010. Radially outward surface 1026 of inner collar 1020 includes one or more notches 1028 configured to match the one or more proximal-distal slots 1072 of actuator 1060 such that inner collar 1020 is prevented from rotating about the longitudinal axis relative to actuator 1060.

Figure 23:
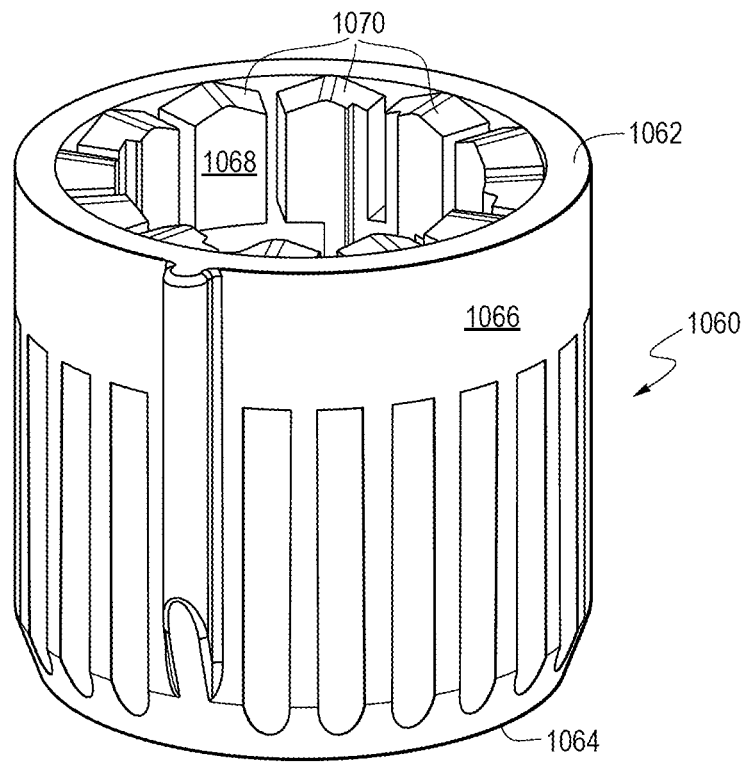
FIG. 23 illustrates a perspective view of the actuator of FIG. 19 with the proximal end of the actuator shown at the top of FIG. 23 and the distal end of the actuator at the bottom of FIG. 23.

The plurality of actuator teeth 1070 as shown in FIG. 23 and plurality of catch teeth 1080 as shown in FIGS. 22 and 25, have a mating geometry such that when actuator 1060 is in the locked configuration, the plurality of actuator teeth 1070 mesh with the plurality of catch teeth 1080. The mating geometry between the plurality of actuator teeth 1070 and the plurality of catch teeth 1080 are such that when the operator applies torque to actuator 1060 or elongate tube 1040, the torque may cause the mating geometry to translate actuator 1060 distally between locked and unlocked configurations without the operator applying distal force. The plurality of actuator teeth 1070 and plurality of catch teeth 1080 may have a non-zero angle or a plurality of detents.

A handle with a locking mechanism as described herein may be used in a number of medical device systems, particularly endoscopes. In particular, the handle of the present disclosure may be used in conjunction with the scopes, devices, and systems described in U.S. patent application Ser. No. 15/445,318 and U.S. patent application Ser. No. 15/445,518, the entire contents of both of which are hereby incorporated by reference in their entireties.

Although the present disclosure has been described with reference to examples and the accompanying drawings, the present disclosure is not limited thereto, but may be variously modified and altered by those skilled in the art to which the present disclosure pertains without departing from the spirit and scope of the present disclosure.

The subject-matter of the disclosure may also relate, among others, to the following aspects:

A first aspect relates to a handle for a medical device, the handle comprising: an actuator configured to move between a locked configuration and an unlocked configuration, the actuator being biased to the locked configuration; a catch configured to engage at least a portion of the actuator; and an elongate tube housing configured to receive an elongate tube, the elongate tube being configured to rotate relative to the handle and defining a longitudinal axis therethrough; wherein, when the actuator is in the unlocked configuration, the actuator is disengaged from the catch, and the elongate tube is rotatable about the longitudinal axis relative to the handle; and wherein, when the actuator is in the locked configuration, the actuator engages with the catch, and the elongate tube is not rotatable about the longitudinal axis relative to the handle.

A second aspect relates to the handle of aspect 1, wherein the catch comprises an outer surface and a protrusion extending outward from the outer surface, wherein when the protrusion contacts the actuator, rotation of the elongate tube relative to the handle is inhibited.

A third aspect relates to the handle of any preceding aspect, wherein the actuator is contacted by a spring.

A fourth aspect relates to the handle of aspect 3, wherein the actuator is biased to the locked configuration.

A fifth aspect relates to the handle of any preceding aspect, wherein the elongate tube is rotatable over a range from greater than 0 degrees to less than 360 degrees relative to the handle.

A sixth aspect relates to the handle of aspect 5, wherein the elongate tube is rotatable relative to the handle over a range from 1 degree to 359 degrees.

A seventh aspect relates to the handle of any preceding aspect, further comprising a bearing disposed in the elongate tube housing, the bearing being configured to ease rotation of the elongate tube relative to the handle.

An eighth aspect relates to the handle of any preceding aspect, wherein the handle comprises a housing, the housing defining a slot for contacting a portion of the actuator.

A ninth aspect relates to the handle of any preceding aspect, wherein the housing is not fixed to the elongate tube, and the elongate tube is rotatable relative to the handle within the housing.

A tenth aspect relates to the handle of any preceding aspect, wherein the catch is configured to engage at least a portion of the actuator by a mating geometry.

An eleventh aspect relates to the handle of aspect 10, wherein the mating geometry comprises a plurality of teeth with a non-zero angle.

A twelfth aspect relates to the handle of aspect 10, wherein the mating geometry comprises a plurality of detents.

A thirteenth aspect relates to the handle of any preceding aspect, wherein the actuator is configured to move between the locked configuration and the unlocked configuration by the application of a non-zero torque to the actuator or the elongate tube.

A fourteenth aspect relates to a scope system, comprising: an elongate tube; and a handle of any preceding aspect.

A fifteenth aspect relates to the handle of aspects 3 and 14, wherein the catch defines a plurality of ridges and a plurality of grooves on the outer surface about a circumference of the outer surface, the plurality of grooves extending radially from the longitudinal axis, each of the plurality of grooves being configured to engage the actuator.

A sixteenth aspect relates to the handle of aspects 3 and 14, wherein the actuator comprises a pin, and the catch defines a plurality of detents about the outer surface, each of the plurality of detents being configured to engage the pin in the locked configuration.

A seventeenth aspect relates to the handle of aspects 3 and 14, wherein the actuator is configured to slide from a proximal position to a distal position, the handle being in the locked configuration when the actuator is disposed in the proximal position, the handle being in the unlocked configuration when the actuator is slid distally to the distal position.

An eighteenth aspect relates to the handle of aspects 3 and 14, wherein the actuator comprises a first magnet and the catch comprises a second magnet, the first magnet being attracted to the second magnet to define the locked configuration.

A nineteenth aspect relates to the handle of aspects 3 and 14, wherein the actuator is configured to swivel to define the unlocked configuration.

In addition to the features mentioned in each of the independent aspects enumerated above, some examples may show, alone or in combination, the optional features mentioned in the dependent aspects and/or as disclosed in the description above and shown in the figures.

What is claimed is:

1. A handle for a medical device, the handle comprising:
   an actuator configured to move distally and proximally between a locked configuration and an unlocked configuration, the actuator being biased proximally to the locked configuration;
   a catch configured to engage at least a portion of the actuator; and
   an elongate tube housing configured to receive an elongate tube, the elongate tube being configured to rotate relative to the handle and defining a longitudinal axis therethrough;

wherein, when the actuator is in the unlocked configuration, the actuator is disengaged from the catch and operatively coupled with the handle, and the elongate tube is rotatable about the longitudinal axis relative to the handle;

wherein, when the actuator is in the locked configuration, the actuator engages with the catch, and the elongate tube is not rotatable about the longitudinal axis relative to the handle; and wherein the actuator is configured to move between the locked configuration and the unlocked configuration and rotate about the longitudinal axis by the application of torque to the actuator or the elongate tube without application of distal force.

2. The handle of claim 1, wherein the actuator is contacted by a spring, and the actuator is biased proximally to the locked configuration.

3. The handle of claim 1, further comprising a bearing disposed between the catch and the elongate tube housing, the bearing being configured to ease rotation of the elongate tube relative to the handle.

4. The handle of claim 1, wherein the catch is configured to engage at least a portion of the actuator by a mating geometry.

5. The handle of claim 1, wherein the catch is configured to engage at least a portion of the actuator by a mating geometry, wherein the mating geometry comprises a plurality of teeth with a non-zero angle.

6. A scope system, comprising:
an elongate tube; and
a handle, comprising:
an actuator configured to move distally and proximally between a locked configuration and an unlocked configuration, the actuator being biased proximally to the locked configuration;
a catch configured to engage at least a portion of the actuator; and
a cavity configured to receive the elongate tube, the elongate tube being configured to rotate relative to the handle and defining a longitudinal axis therethrough;
wherein, when the actuator is in the unlocked configuration, the actuator is disengaged from the catch and operatively coupled with the handle, and the elongate tube is rotatable about the longitudinal axis relative to the handle;
wherein, when the actuator is in the locked configuration, the actuator engages with the catch, and the elongate tube is not rotatable about the longitudinal axis relative to the handle; and
wherein the actuator is configured to move between the locked configuration and the unlocked configuration and rotate about the longitudinal axis by the application of torque to the actuator or the elongate tube without application of distal force.

7. The handle of claim 6, wherein the actuator is contacted by a spring, and the actuator is biased proximally to the locked configuration.

\* \* \* \* \*